(12) United States Patent
Liu et al.

(10) Patent No.: US 10,683,246 B2
(45) Date of Patent: Jun. 16, 2020

(54) METHOD AND SYSTEM FOR LIGHT OLEFIN SEPARATION

(71) Applicant: UOP LLC, Des Plaines, IL (US)

(72) Inventors: Chunqing Liu, Arlington Heights, IL (US); Lubo Zhou, Inverness, IL (US); Stanley J. Frey, Palatine, IL (US); Gregory R. Werba, Arlington Heights, IL (US); Carl W. Liskey, Chicago, IL (US); Simon E. Albo, Evanston, IL (US); Trung Pham, Mount Prospect, IL (US)

(73) Assignee: UOP LLC, Des Plaines, IL (US)

(*) Notice: Subject to any disclaimer, the term of this patent is extended or adjusted under 35 U.S.C. 154(b) by 0 days.

(21) Appl. No.: 16/058,784

(22) Filed: Aug. 8, 2018

(65) Prior Publication Data

US 2019/0100479 A1 Apr. 4, 2019

Related U.S. Application Data

(60) Provisional application No. 62/566,427, filed on Sep. 30, 2017.

(51) Int. Cl.
| | |
|---|---|
| *B01D 3/00* | (2006.01) |
| *C07C 7/00* | (2006.01) |
| *B01D 3/14* | (2006.01) |
| *B01D 53/22* | (2006.01) |
| *C07C 7/144* | (2006.01) |
| *B01D 71/06* | (2006.01) |
| *B01D 69/14* | (2006.01) |
| *C07C 7/04* | (2006.01) |

(52) U.S. Cl.
CPC .............. *C07C 7/005* (2013.01); *B01D 3/007* (2013.01); *B01D 3/145* (2013.01); *B01D 53/225* (2013.01); *B01D 53/228* (2013.01); *B01D 53/229* (2013.01); *B01D 69/148* (2013.01); *B01D 71/06* (2013.01); *C07C 7/04* (2013.01); *C07C 7/144* (2013.01); *B01D 2256/24* (2013.01); *B01D 2257/702* (2013.01)

(58) Field of Classification Search
CPC ...... B01D 3/007; B01D 3/145; B01D 53/225; B01D 53/228; B01D 53/229; B01D 69/148; B01D 71/06
See application file for complete search history.

(56) References Cited

U.S. PATENT DOCUMENTS

| | | | | |
|---|---|---|---|---|
| 5,131,928 A | * | 7/1992 | Blackman | B01D 53/22 210/500.41 |
| 7,070,694 B2 | * | 7/2006 | Colling | B01D 3/14 203/19 |
| 7,361,800 B2 | * | 4/2008 | Herrera | B01D 53/228 585/809 |
| 8,475,567 B2 | * | 7/2013 | Cougard | C07C 7/04 203/57 |

(Continued)

*Primary Examiner* — Jonathan Miller

(57) ABSTRACT

A process is provided for separation of light olefins and paraffins and particular for the separation of propylene and propane comprising sending at least one olefin/paraffin stream to a distillation column and a membrane unit to produce an olefin stream comprising at least 92 mol % olefin. In an embodiment of the invention where the membrane unit is placed downstream from the column which can produce propylene streams at polymer grade of over 99.5 mol % propylene.

14 Claims, 2 Drawing Sheets

(56) References Cited

U.S. PATENT DOCUMENTS

| | | | |
|---|---|---|---|
| 9,120,882 B2* | 9/2015 | Janssens | C08F 6/001 |
| 2004/0182786 A1* | 9/2004 | Colling | B01D 3/14 |
| | | | 210/640 |
| 2008/0167512 A1* | 7/2008 | Sanders | B01D 53/226 |
| | | | 585/818 |
| 2011/0049051 A1* | 3/2011 | Cougard | C07C 7/04 |
| | | | 210/640 |
| 2015/0053079 A1* | 2/2015 | Koros | B01D 53/228 |
| | | | 95/50 |
| 2015/0141726 A1* | 5/2015 | Thakkar | C10G 45/02 |
| | | | 585/330 |
| 2017/0203230 A1* | 7/2017 | Raiser | B01D 3/145 |
| 2017/0354918 A1* | 12/2017 | Liu | B01D 69/12 |

* cited by examiner

METHOD AND SYSTEM FOR LIGHT OLEFIN SEPARATION

CROSS-REFERENCE TO RELATED APPLICATION

This application claims priority from U.S. Provisional Application No. 62/566,427 filed Sep. 30, 2017, the contents of which cited application are hereby incorporated by reference in its entirety.

BACKGROUND OF THE INVENTION

Over 170 Separex™ membrane systems have been installed in the world for gas separation applications such as for the removal of acid gases from natural gas, in enhanced oil recovery, and hydrogen purification. Two new Separex™ membranes (Flux+ and Select) have been commercialized recently by Honeywell UOP, Des Plaines, Ill. for carbon dioxide removal from natural gas. These Separex™ spiral wound membrane systems currently hold the membrane market leadership for natural gas upgrading. These membranes, however, do not have outstanding performance for olefin/paraffin separations. Development of new stable and very high selectivity membranes is critical for the future success of membranes for olefin/paraffin separation applications such as propylene/propane and ethylene/ethane separations.

Light olefins, such as propylene and ethylene, are produced as co-products from a variety of feedstocks in a number of different processes in the chemical, petrochemical, and petroleum refining industries. Various petrochemical streams contain olefins and other saturated hydrocarbons. Typically, these streams are from stream cracking units (ethylene production), catalytic cracking units (motor gasoline production), or the dehydrogenation of paraffins.

Currently, the separation of olefin and paraffin components is performed by cryogenic distillation, which is expensive and energy intensive due to the low relative volatilities of the components. Large capital expense and energy costs have created incentives for extensive research in this area of separations, and low energy-intensive membrane separations have been considered as an attractive alternative.

In principle, membrane-based technologies have the advantages of both low capital cost and high-energy efficiency compared to conventional separation methods for olefin/paraffin separations, such as propylene/propane and ethylene/ethane separations. Four main types of membranes have been reported for olefin/paraffin separations. These are facilitated transport membranes, polymer membranes, mixed matrix membranes, and inorganic membranes. Facilitated transport membranes, or ion exchange membranes, which sometimes use silver ions as a complexing agent, have very high olefin/paraffin separation selectivity. However, poor chemical stability, due to carrier poisoning or loss, high cost, and low flux, currently limit practical applications of facilitated transport membranes.

Separation of olefins from paraffins via conventional polymer membranes has not been commercially successful due to inadequate selectivities and permeabilities of the polymer membrane materials, as well as due to plasticization issues. Polymers that are more permeable are generally less selective than are less permeable polymers. A general trade-off has existed between permeability and selectivity (the so-called "polymer upper bound limit") for all kinds of separations, including olefin/paraffin separations. In recent years, substantial research effort has been directed to overcoming the limits imposed by this upper bound. Various polymers and techniques have been used, but without much success in terms of improving the membrane selectivity.

More efforts have been undertaken to develop metal ion incorporated, high olefin/paraffin selectivity facilitated transport membranes. The high selectivity for olefin/paraffin separations is achieved by the incorporation of metal ions such as silver (I) or copper (I) cations into the solid nonporous polymer matrix layer on top of the highly porous membrane support layer (so-called "fixed site carrier facilitated transport membrane") or directly into the pores of the highly porous support membrane (so-called "supported liquid facilitated transport membrane") that results in the formation of a reversible metal cation complex with the pi bond of olefins, whereas no interaction occurs between the metal cations and the paraffins. Addition of water, plasticizer, or humidification of the olefin/paraffin feed streams to either the fixed site carrier facilitated transport membranes or the supported liquid facilitated transport membranes is usually required to obtain reasonable olefin permeances and high olefin/paraffin selectivities. The performance of fixed site carrier facilitated transport membranes is much more stable than that of the supported liquid facilitated transport membranes and the fixed site carrier facilitated transport membranes are less sensitive to the loss of metal cation carriers than the supported liquid facilitated transport membranes.

Refinery grade propylene separation involves conventional distillation columns. For customers who want to debottleneck or expand capacity without having to install additional columns, the present invention provides a membrane solution that can process additional capacity required and selectively separate propylene from propane to produce very high purity propylene. The membrane solution can be cost effective and offer flexibility for customers with faster startup than conventional column installations. The payback time (based on lower investment) is also a very attractive solution for processing additional throughput.

It has been found that effective processing of olefin/paraffin streams can be accomplished with membranes. A modular approach can also be of great advantage for skid-built, low installation factor and faster startup than conventional column systems.

For an existing distillation system to produce 200 KMTA (metric tons per year) propylene (refinery grade 93 mol %), the column diameter is expected to be 3.96 meters (13 feet) with 140 trays in one embodiment. To debottleneck this system, a membrane system with 200-1000 elements, preferably 400-700, can be installed to bring in additional 136 KMTA propylene, making a total of 336 KMTA for the customer. In order to achieve the same additional capacity by using the prior art distillation column technology, a new column of 11 feet can be used.

The erected cost for a new column system is estimated to be more than double the cost of a new membrane system. The payback time for the above example is 3-6 months, which is about twice lower compared to the payback from the equivalent column system. Even with compression, the operating costs remain equivalent to the column system in which there would be two columns as compared to the single column plus the membrane system in the present invention.

The feed to the membrane system can be an effluent stream from a propane dehydrogenation (PDH) process, a FCC process or other source of a light olefin stream with various concentration of propylene, ranging from 30-70 mol %. This stream is contacted with a membrane separation unit. The permeate from the membrane system is propylene rich and has a high concentration of propylene, 93-99% or higher and in some embodiments of the invention from 95-98%. The flow rate of the permeate stream is 25-50% of the feed stream, or preferably 30-40%. The retentate stream can be compressed up to 220-250 psig and then sent to a C3 splitter column.

The distillation column is typically operated at 150-250 psig, preferably at 180-230 psig. Lower pressure can be achieved, however, condensing the vapor overhead at the top of the column which may require chilled water, if available. In some embodiments, the feed to the column may pass through a shared drier system to reduce water before contacting with the column. The column condenser temperature is 32.2 to 48.9° C. (90-120° F.), preferably 37.8 to 43.3° C. (100° to 110° F.) (optimized for cooling water condensing). The reboiler temperature is 37.8° to 60° C. (100° to 140° F.), preferably 43.3° to 51.7° C. (110° to 125° F.). For new units, the technology that the tray spacing can be optimized so tray spacing is less than 20 inches, increase efficiency with less overall height (up to 30% height reduction compared to regular trays). The composition of the distillate is 80-98 mol % propylene, or 88-95 mol % propylene in some instances. The recovery of propylene through the column is 90-98%, or preferably 93-96%.

The permeate from the membrane (95-99 mol % C3=) can be mixed with the distillate stream (88-95%) to produce a refinery grade propylene product stream. The propylene product stream may go through a shared drier to remove water.

For an existing Oleflex or PDH system, a portion up to all of the retentate can be compressed and contacted with a secondary membrane system to further produce a second permeate (95-99 mol % propylene) and a second retentate (>75 mol % propane) that can be compressed and recycled to the reactor system to further convert to propylene. In any embodiments, the bottom of the distillation column, which has greater than 90 mol % propane, can be recycled back to the dehydrogenation unit. The above discussion is mainly concerning a membrane unit or system placed in front of an existing column to result in a system that can produce about 93 mol % propylene. It has also been found that a system can be installed with the membrane system placed after the column and then produce even higher levels of propylene in its product stream.

SUMMARY OF THE INVENTION

The invention provides a process for separation of propylene and propane comprising sending at least one hydrocarbon stream to a distillation column and a membrane unit to produce a light olefin stream such as a propylene stream comprising at least 92 mol % propylene. The hydrocarbon stream that is processed may be a C3 stream comprising between about 25-75 mol % propylene. In some instances, the C3 stream may comprise 35-65 mol % propylene. The process may involve at least one C3 stream first passing to the distillation column to produce an upper stream comprising about 75 mol % propylene and a bottom stream comprising at least 90 mol % propane and then sending the upper stream to a membrane unit to separate the upper stream into a permeate stream comprising at least 95-98 mol % propylene and a retentate stream comprising propane. In preferred embodiments of the invention, the membrane unit comprises a plurality up to 1,000 or more membranes wherein the membranes are facilitated transport membranes. The facilitated transport membranes comprise a solid nonporous polymer matrix layer on top of a nanoporous support membrane.

In addition, the facilitated transport membranes comprise metal ions incorporated into the nonporous polymer matrix layer and the nanopores on the skin layer surface of the nanoporous support membrane.

The process of this invention is able to process olefin streams having differing concentrations of olefins such as propylene as can be found in the product of different olefin production processes. For example, one of the streams may comprise about 25-45 mol % propylene and one of the streams may comprise about 50-70 mol % propylene. The process of the present invention may produce a product stream that is polymer grade and contains about 99.3-99.8 mol % propylene.

The process can also be used to separate hydrocarbons where there are other paraffins and olefins such as C4 and C5 hydrocarbons. Advantages of the process include the ability to employ a smaller diameter distillation column or treat a greater volume of hydrocarbons to a lower purity while the lower costing membrane unit completing the purification.

DETAILED DESCRIPTION OF THE INVENTION

Figure 1:
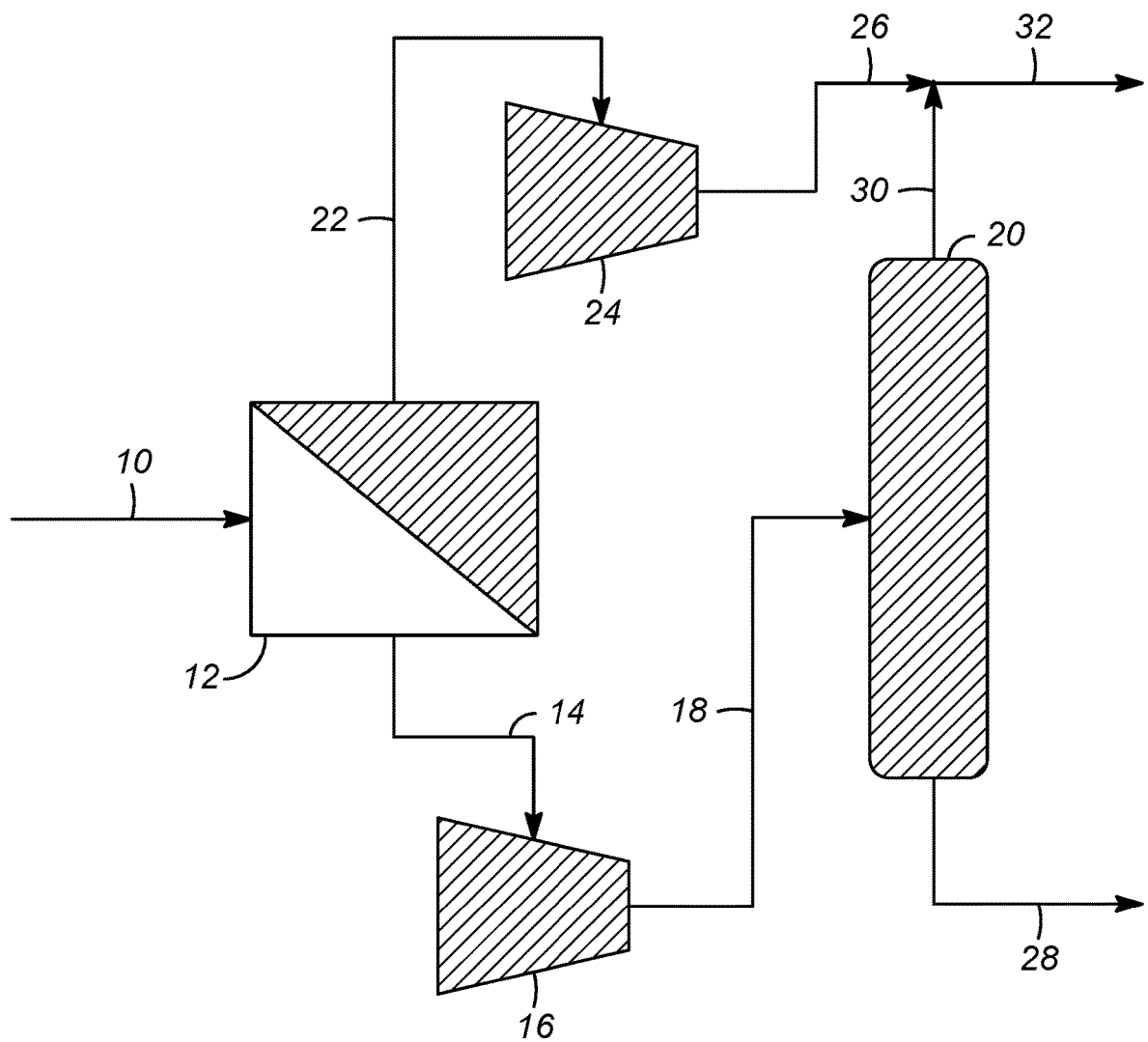
FIG. 1 shows an embodiment of the invention with an olefin flow stream passing first through a membrane unit and then through a distillation column to separate olefins and paraffins.

The membrane technology of the present invention offers the capability of upgrading propylene from 75% purity or less to polymer grade 99.5% with the membranes and element design (1500-3000 elements depending on product capacity). For a distillation column, the overhead stream needs only be rectified to 75% or up to 90% and then further purified by the membranes to get to polymer grade product. By reducing the overhead purity, the reflux ratio decreases substantially, the reboiler duty also decreases, and the column diameter and height can also be reduced for a new design. For revamp cases, the same shell diameter can accommodate more feed to increase throughput or product capacity. Also, the overhead compression ratio decreases, requiring only single stage compressor (final pressure is 200-240 psig).

Although the main object of the present invention is to separate propane and propylene, additional capacity may be added to separate C2, C4, as well as C5 mixtures.

The present invention is made possible by the use of recently developed membranes including those described in US 2017/0354918 A1; U.S. application Ser. No. 15/615,134 filed Jun. 6, 2017; US 2018/0001277 A1; US 2018/0001268 A1; and U.S. application Ser. No. 15/599,258 filed May 18, 2017 incorporated herein in their entireties.

US 2017/0354918 A1 disclosed a facilitated transport membrane comprising a relatively hydrophilic, very small pore, nanoporous support membrane, a hydrophilic polymer inside the very small nanopores on the skin layer surface of the support membrane, a thin, nonporous, hydrophilic polymer layer coated on the surface of the support membrane, and metal salts incorporated in the hydrophilic polymer layer coated on the surface of the support membrane and the hydrophilic polymer inside the very small nanopores, a method of making this membrane, and the use of this membrane for olefin/paraffin separations, particularly for C3=/C3 and C2=/C2 separations. The relatively hydrophilic, very small pore, nanoporous support membrane used for the preparation of the new facilitated transport membrane comprising a relatively hydrophilic, very small pore, nanoporous support membrane, a hydrophilic polymer inside the very small nanopores on the surface of the support membrane, a thin, nonporous, hydrophilic polymer layer coated on the surface of said support membrane, and metal salts incorporated in the hydrophilic polymer layer coated on the surface of the support membrane and said hydrophilic polymer inside the very small nanopores disclosed in the present invention comprises a relatively hydrophilic polymer selected from a group consisting of, but is not limited to, polyethersulfone (PES), a blend of PES and polyimide, cellulose acetate, cellulose triacetate, and a blend of cellulose acetate and cellulose triacetate. The relatively hydrophilic, very small pore, nanoporous support membrane described in the current invention has an average pore diameter of less than 10 nm on the membrane skin layer surface. The relatively hydrophilic, very small pore, nanoporous support membrane described in the current invention can be either asymmetric integrally skinned membrane or thin film composite (TFC) membrane with either flat sheet (spiral wound) or hollow fiber geometry.

The hydrophilic polymer inside the very small nanopores on the surface of the relatively hydrophilic, very small pore, nanoporous support membrane of the facilitated transport membrane described in US 2017/0354918 A1 can be selected from, but is not limited to, a group of hydrophilic polymers containing chitosan, sodium carboxylmethyl-chitosan, carboxylmethyl-chitosan, hyaluronic acid, sodium hyaluronate, carbopol, polycarbophil calcium, poly(acrylic acid) (PAA), poly(methacrylic acid) (PMA), sodium alginate, alginic acid, poly(vinyl alcohol) (PVA), poly(ethylene oxide) (PEO), poly(ethylene glycol) (PEG), poly(vinylpyrrolidone) (PVP), gelatin, carrageenan, sodium lignosulfonate, and mixtures thereof.

The metal salts incorporated in the hydrophilic polymer layer coated on the surface of said support membrane and the hydrophilic polymer inside the very small nanopores of the facilitated transport membrane described in US 2017/0354918 A1 are preferred to be selected from silver salts or copper salts, such as silver(I) nitrate or copper(I) chloride.

The dried, relatively hydrophilic, very small pore, nanoporous support membrane comprising hydrophilic polymers inside the very small nanopores on the membrane surface described in US 2017/0354918 A1 has carbon dioxide permeance of 800-10,000 GPU and no carbon dioxide/methane selectivity at 50° C. under 30-100 psig 10% $CO_2$/90% $CH_4$ mixed gas feed pressure.

Some of the facilitated transport membranes described in US 2018/0001277 A1 are useful in the present invention. One high performance facilitated transport membrane 1.5MAg+/PI-50 that may be used has an asymmetric integrally skinned flat sheet membrane structure was fabricated from carboxylic acid containing poly(2,2'-bis-(3,4-dicarboxyphenyl) hexafluoropropane dianhydride-3,5-diaminobenzoic acid-3,3'-dihydroxy-4,4'-diamino-biphenyl) polyimide (abbreviated as PI-50) that was synthesized from 2,2'-bis-(3,4-dicarboxyphenyl) hexafluoropropane dianhydride (6 FDA) and a mixture of 3,5-diaminobenzoic acid (3,5-DBA) and 3,3'-dihydroxy-4,4'-diamino-biphenyl (HAB) (molar ratio of 3,5-DBA/HAB=1:4), wherein the carboxylic acid functional groups on PI-50 were ion-exchanged or chelated with silver (I) cation. Permeation testing experiments using humidified (relative humidity 80-100%) propylene and propane mixed vapor phase feed (30% propylene and 70% propane at 791 kPa (100 psig) and 35° C.) showed that this 1.5MAg+/PI-50 membrane had both high propylene (C3=) permeance ($P_{C3=}/L$=259 GPU) and high propylene/propane (C3=/C3) selectivity ($\alpha_{C3=/C3}$=466). Permeation testing experiments using humidified (relative humidity 80-100%) propylene and propane mixed vapor phase feed (70% propylene and 30% propane at 791 kPa (100 psig) and 35° C.) also showed that this 1.5MAg+/PI-50 membrane had both high propylene (C3=) permeance ($P_{C3=}/L$=192 GPU) and high propylene/propane (C3=/C3) selectivity ($\alpha_{C3=/C3}$=1000).

Another new high performance facilitated transport membrane 3MAg+/PI-150 that may be used is an asymmetric integrally skinned membrane flat sheet structure that was fabricated from carboxylic acid containing poly(2,2'-bis-(3,4-dicarboxyphenyl) hexafluoropropane dianhydride-3,5-diaminobenzoic acid-3,3',5,5'-tetramethyl-4,4'-methylene dianiline) polyimide (abbreviated as PI-150) derived from the polycondensation reaction of 6 FDA and a mixture of 3,5-DBA and 3,3',5,5'-tetramethyl-4,4'-methylene dianiline (TMMDA) (molar ratio of 3,5-DBA/TMMDA=2:1), wherein the carboxylic acid functional groups on PI-150 were ion-exchanged or chelated with silver cation. Permeation testing experiments using humidified (relative humidity 80-100%) propylene and propane mixed vapor phase feed (30% propylene and 70% propane at 791 kPa (100 psig) and 35° C.) showed that this 3MAg+/PI-150 membrane has both high propylene (C3=) permeance ($P_{C3=}/L$=147 GPU) and high propylene/propane (C3=/C3) selectivity ($\alpha_{C3=/C3}$=239).

The facilitated transport membrane that is used may comprise a carboxylic acid functional group containing polyimide wherein the carboxylic acid functional groups are ion-exchanged or chelated with metal cations such as silver (I) or copper (I) cations. The metal cation ion-exchanged or chelated carboxylic acid functional group containing polyimide described in U.S. application Ser. No. 15/610,305 comprising a plurality of repeating units of formula (I)

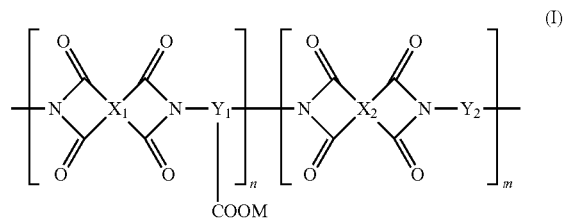

wherein $X_1$ and $X_2$ are selected from the group consisting of

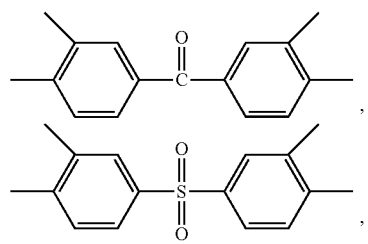

-continued
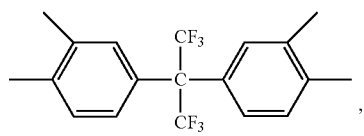
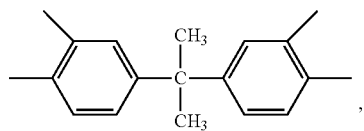
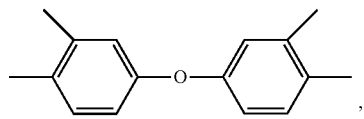
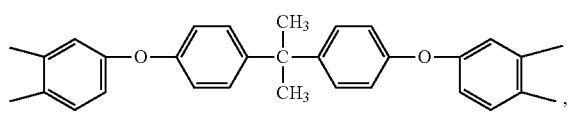
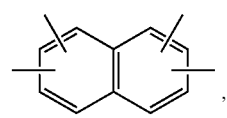
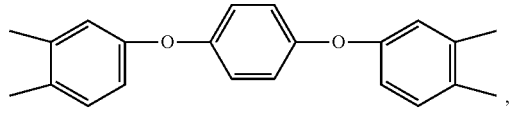
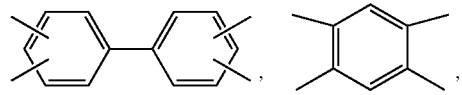
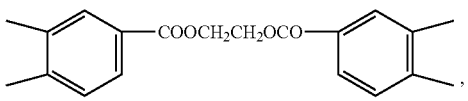
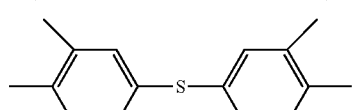
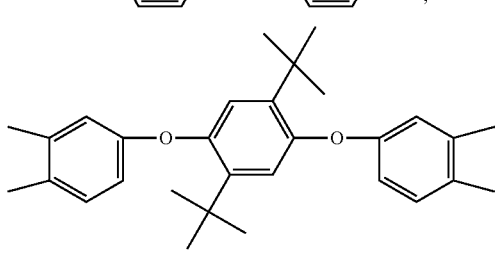
and mixtures thereof, and wherein X1 and X2 may be the same or different from each other; wherein $Y_1$—COOM is selected from the group consisting of
-continued
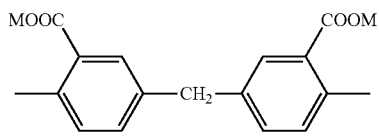
and mixtures thereof and wherein M is selected from silver (I) cation or copper (I) cation; wherein Y2 is selected from the group consisting of
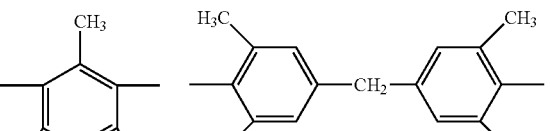
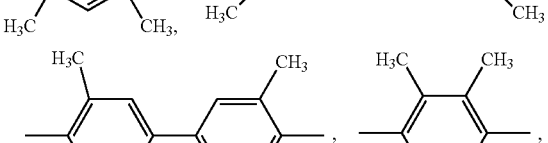
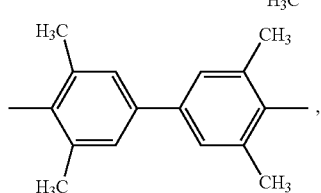
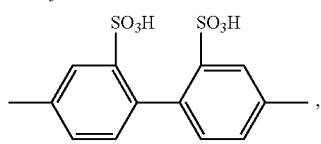
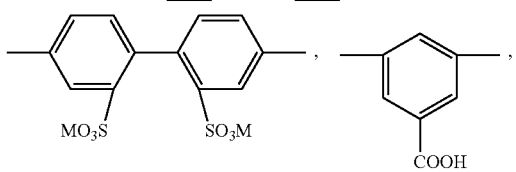
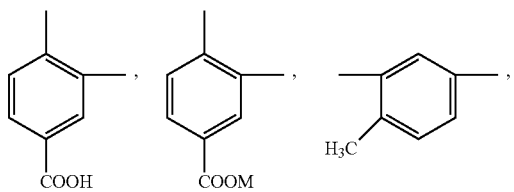
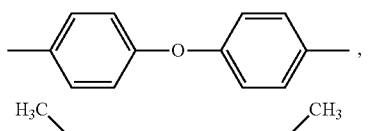
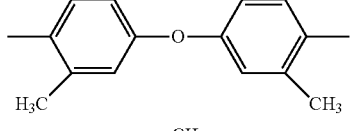
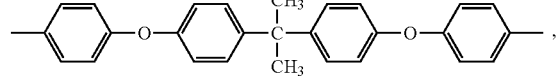

-continued

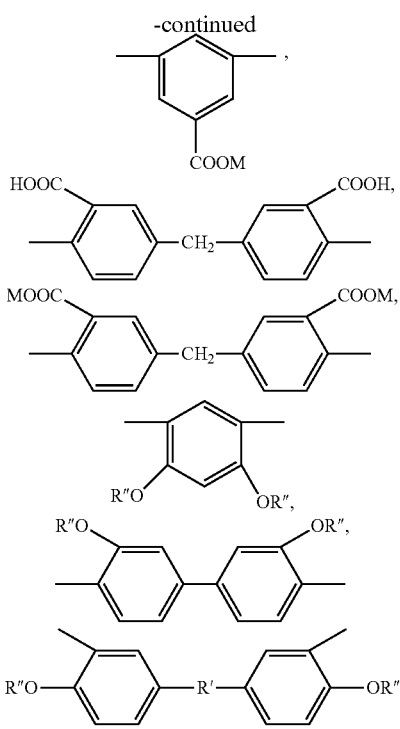

and mixtures thereof, and —R'— is selected from the group consisting of

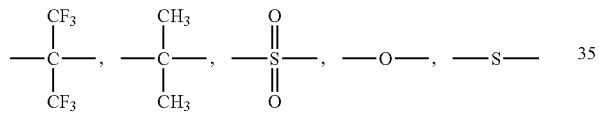

and mixtures thereof, and —R"— is selected from the group consisting of —H, COCH$_3$, and mixtures thereof, and M is selected from silver (I) cation or copper (I) cation; wherein n and m are independent integers from 2 to 500; and wherein n/m is in a range of 1:0 to 1:10, and preferably n/m is in a range of 1:0 to 1:5.

Preferably, X$_1$ and X$_2$ are selected from the group consisting of

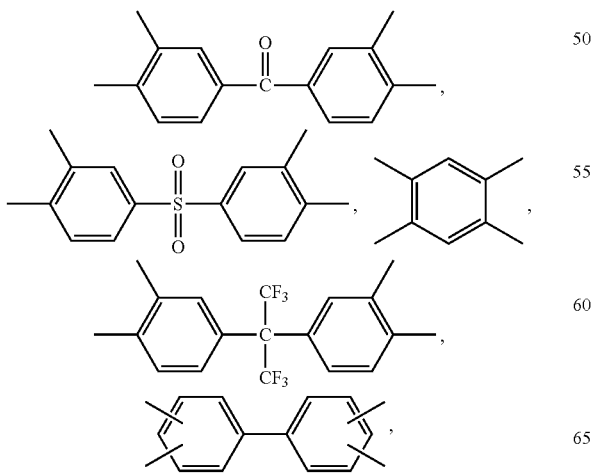

-continued

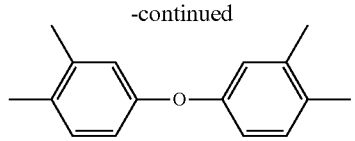

and mixtures thereof, and wherein X1 and X2 may be the same or different from each other; preferably Y$_1$—COOM is selected from the group consisting of

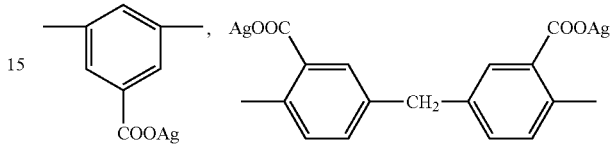

and mixtures thereof; preferably Y2 is selected from the group consisting of

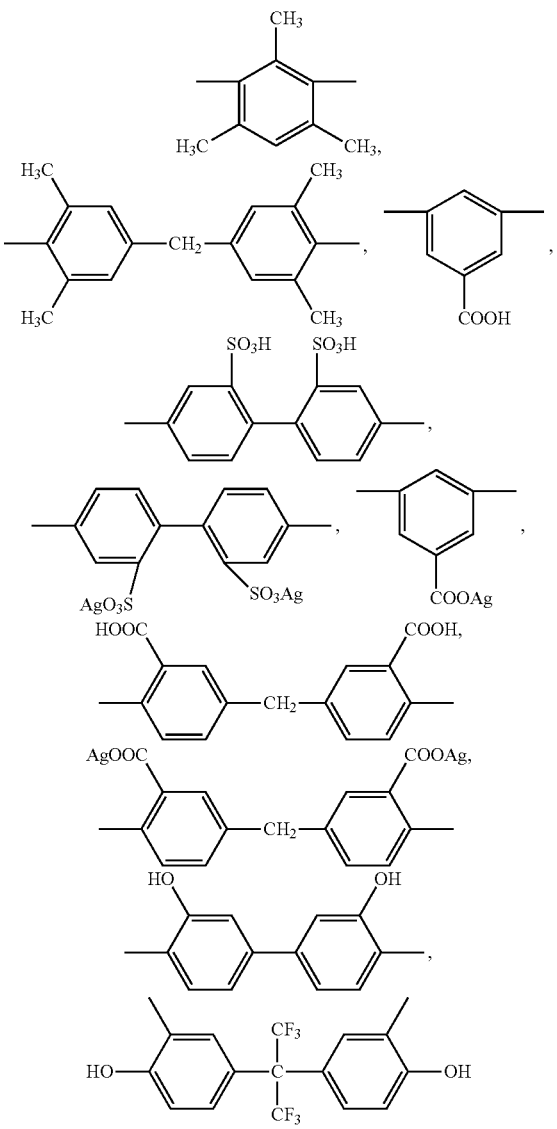

and mixtures thereof.

FIG. 1 shows a membrane/column system in which a hydrocarbon stream comprising about 65 mol % propylene enters a membrane unit 12. A permeate 22 exits membrane unit 12 and may be compressed by compressor 24 to produce a compressed propylene product stream 26 that then is combined with propylene product stream 30 with combined propylene product stream 32 which has about a 92-95 mol % level of propylene. A retentate stream that is primarily propane passes through line 14 to compressor 16. A compressed retentate stream 18 is shown entering distillation column 20. A propane-rich stream 28 exits the bottom of distillation column 20 and a propylene stream 30 exits the top of distillation column 20 to be combined with propylene product stream 26 with combined propylene product stream 32 having a purity of about 92-95 mol % propylene with up to 95-97 mol % propylene possible.

Figure 2:
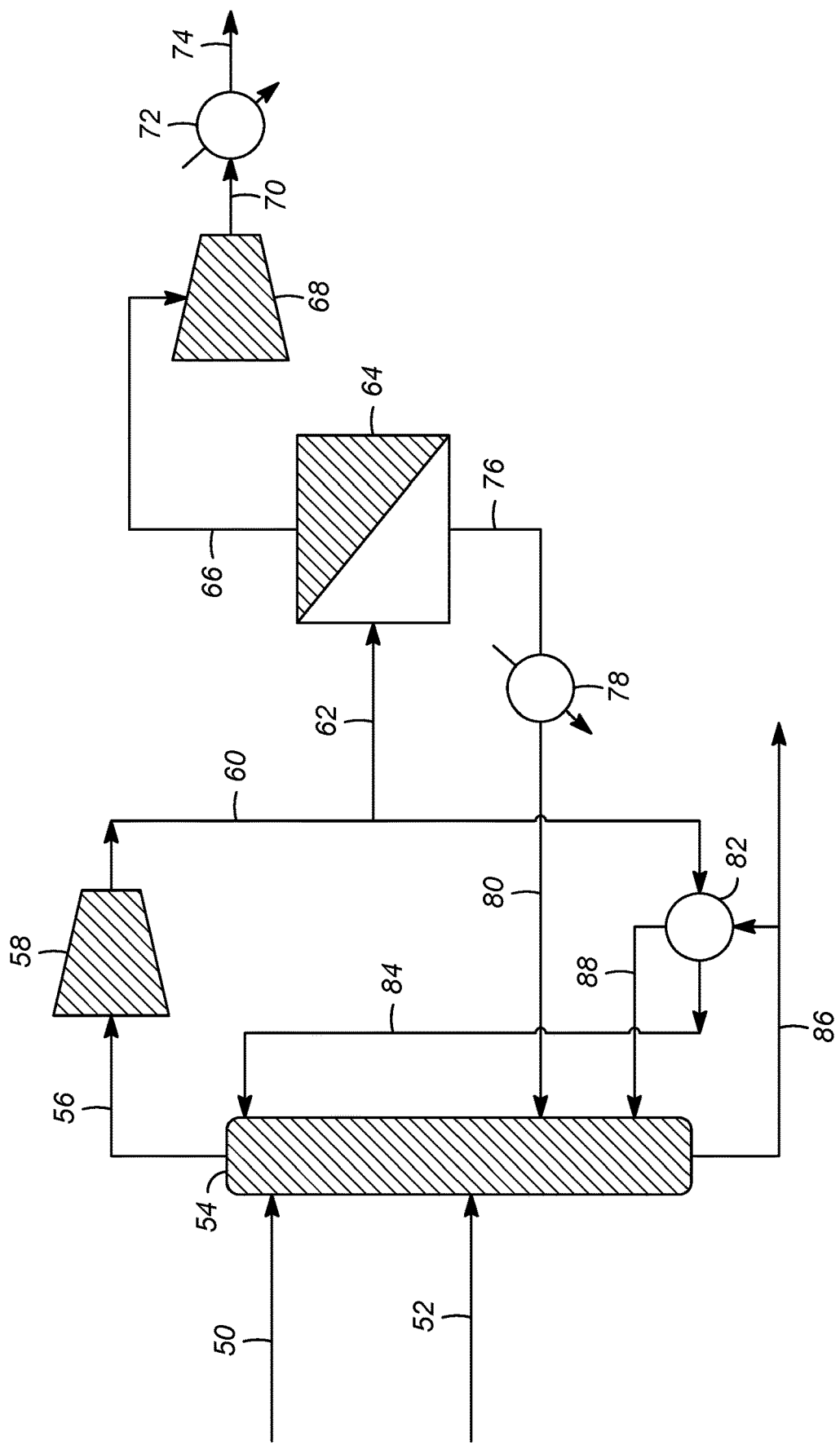
FIG. 2 shows an embodiment of the invention with one or more olefin flow streams first entering a distillation column and then passing through a membrane unit to separate olefins and paraffins.

FIG. 2 shows an alternative embodiment of a system that includes a distillation column and a membrane unit for separating propane and propylene. There are two feed streams 50 and 52 shown that contain different concentrations of propylene. For example, feed stream 50 may contain about 60-70 mol % propylene and feed stream 52 may contain about 25-45 mol % propylene. These two feed streams enter distillation column 54 that is a C3 splitter with a propane stream 86 exiting the bottom while a portion of propane stream 86 may be split off to be reboiled through heat exchanger 82. A partially purified propylene stream 56 that is about 72-90 mol % propylene is sent to compressor 58 and then compressed partially purified propylene stream 60 and then 62 is sent to membrane unit 64 with a purified permeate stream 66 being compressed in compressor 68 to produce a compressed permeate stream 70 which passes through heat exchanger 72 and on as product stream 74 that may be as high as polymer grade 99.3-99.8 mol % propylene. A portion of compressed partially purified propylene stream 60 may be recycled and cooled in heat exchanger 82 and returned to distillation column 54 through line 84. A retentate stream that is mostly propane is shown exiting membrane unit 64 through line 76, cooled in heat exchanger or chiller 78 and returning to distillation column 54 through line 80.

Specific Embodiments

While the following is described in conjunction with specific embodiments, it will be understood that this description is intended to illustrate and not limit the scope of the preceding description and the appended claims.

A first embodiment of the invention is a process for separation of olefin and paraffin mixtures comprising sending at least one hydrocarbon stream to a distillation column and a membrane unit to produce an olefin stream comprising at least 92 mol % olefin. An embodiment of the invention is one, any or all of prior embodiments in this paragraph up through the first embodiment in this paragraph wherein the at least one hydrocarbon stream comprises between 25-90 mol % olefin. An embodiment of the invention is one, any or all of prior embodiments in this paragraph up through the first embodiment in this paragraph wherein the at least one hydrocarbon stream first passes to the distillation column to produce an upper stream more concentrated in olefin than the at least one hydrocarbon stream and a bottom stream more concentrated in paraffin than the hydrocarbon stream and then sending a portion of the upper stream to a membrane unit to separate the upper stream into a permeate stream comprising at least 90-98 mol % olefin and a retentate stream comprising paraffin. An embodiment of the invention is one, any or all of prior embodiments in this paragraph up through the first embodiment in this paragraph wherein the membrane unit comprises a plurality of membranes wherein the membranes are facilitated transport membranes. An embodiment of the invention is one, any or all of prior embodiments in this paragraph up through the first embodiment in this paragraph wherein the facilitated transport membranes comprise a solid nonporous polymer matrix layer on top of a nanoporous support membrane. An embodiment of the invention is one, any or all of prior embodiments in this paragraph up through the first embodiment in this paragraph wherein the facilitated transport membranes comprise metal ions incorporated into the nonporous polymer matrix layer and the nanopores on the skin layer surface of the nanoporous support membrane. An embodiment of the invention is one, any or all of prior embodiments in this paragraph up through the first embodiment in this paragraph wherein the at least one hydrocarbon stream comprise at least two streams comprising different concentrations of olefin. An embodiment of the invention is one, any or all of prior embodiments in this paragraph up through the first embodiment in this paragraph wherein one of the streams comprises about 25-45 mol % olefin and one of the streams comprises about 50-70 mol % olefin. An embodiment of the invention is one, any or all of prior embodiments in this paragraph up through the first embodiment in this paragraph wherein the permeate stream comprises about 99.3-99.8 mol % olefin. An embodiment of the invention is one, any or all of prior embodiments in this paragraph up through the first embodiment in this paragraph wherein at least a portion of the retentate stream is recycled to the distillation column to separate the retentate stream into a paraffin stream and an olefin stream. An embodiment of the invention is one, any or all of prior embodiments in this paragraph up through the first embodiment in this paragraph wherein the hydrocarbon stream comprises C3 or C4 olefin and paraffin hydrocarbons. An embodiment of the invention is one, any or all of prior embodiments in this paragraph up through the first embodiment in this paragraph wherein the olefin is propylene, wherein the paraffin is propane, and wherein the hydrocarbon stream comprises propylene and propane hydrocarbons. An embodiment of the invention is one, any or all of prior embodiments in this paragraph up through the first embodiment in this paragraph wherein the olefin is ethylene, wherein the paraffin is ethane, and wherein the hydrocarbon stream comprises ethylene and ethane hydrocarbons. An embodiment of the invention is one, any or all of prior embodiments in this paragraph up through the first embodiment in this paragraph wherein the olefin is C4 olefin, wherein the paraffin is C4 paraffin, and wherein the hydrocarbon stream comprises C4 olefin and C4 paraffin hydrocarbons. An embodiment of the invention is one, any or all of prior embodiments in this paragraph up through the first embodiment in this paragraph wherein the upper stream contains <0.05% C4 olefins in the total olefins. An embodiment of the invention is one, any or all of prior embodiments in this paragraph up through the first embodiment in this paragraph wherein the permeate stream is compressed and then condensed with cooling water. An embodiment of the invention is one, any or all of prior embodiments in this paragraph up through the first embodiment in this paragraph wherein at least a portion of the retentate stream is condensed to liquid before recycling to the distillation column. An embodiment of the invention is one, any or all of prior embodiments in this paragraph up through the first embodiment in this paragraph wherein the portion of the upper stream that is not sent to the membrane is recycled to the distillation column after condensation. An embodiment of the invention is one, any or all of prior embodiments in this paragraph up through the first embodiment in this paragraph wherein the condensation of the upper stream not sent to the membrane is done via heat exchange with the distillation column bottom material supplying heat duty for the reboiler. An embodiment of the invention is one, any or all of prior embodiments in this paragraph up through the first embodiment in this paragraph wherein at least a portion of the retentate stream is returned to the distillation column below the point of return of the upper stream that is not sent to the membrane. An embodiment of the invention is one, any or all of prior embodiments in this paragraph up through the first embodiment in this paragraph wherein the distillation column has a lower reboiler duty than in a system comprising a distillation column without a membrane unit.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for separation of olefin and paraffin mixtures comprising sending at least one hydrocarbon stream to a distillation column to produce an upper stream more concentrated in olefin than said at least one hydrocarbon stream and a bottom stream more concentrated in paraffin than the at least one hydrocarbon stream and sending a portion of said upper stream in vapor phase comprising 72-90% olefin to a membrane unit to separate said upper stream into a permeate stream in vapor phase comprising at least 99 mol % olefin and a retentate stream in vapor phase comprising paraffin, wherein the portion of the upper stream is recycled to the distillation column after condensation, wherein said membrane unit comprises a plurality of membranes which are facilitated transport membranes comprising a solid nonporous polymer matrix layer on top of a nanoporous support membrane.

2. The process of claim 1 wherein said facilitated transport membranes comprise metal ions incorporated into said nonporous polymer matrix layer and nanopores on a skin layer surface of said nanoporous support membrane.

3. The process of claim 1 wherein said at least one hydrocarbon stream comprise at least two streams comprising different concentrations of olefin.

4. The process of claim 1 wherein said permeate stream comprises about 99.8 mol % olefin.

5. The process of claim 1 wherein at least a portion of said retentate stream is recycled to said distillation column to separate said retentate stream into a paraffin stream and an olefin stream.

6. The process of claim 1 wherein said hydrocarbon stream comprises C3 or C4 olefin and paraffin hydrocarbons.

7. The process of claim 1 wherein said olefin is propylene, wherein said paraffin is propane, and wherein said hydrocarbon stream comprises propylene and propane hydrocarbons.

8. The process of claim 1 wherein said olefin is ethylene, wherein said paraffin is ethane, and wherein said hydrocarbon stream comprises ethylene and ethane hydrocarbons.

9. The process of claim 1 wherein said olefin is C4 olefin, wherein said paraffin is C4 paraffin, and wherein said hydrocarbon stream comprises C4 olefin and C4 paraffin hydrocarbons.

10. The process of claim 1 wherein the upper stream contains <0.05% C4 olefins in the total olefins.

11. The process of claim 1 wherein the permeate stream is compressed and then condensed with cooling water.

12. The process of claim 5 wherein at least a portion of the retentate stream is condensed to liquid before recycling to the distillation column.

13. The process of claim 11 wherein the condensation of the upper stream not sent to the membrane is done via heat exchange with the distillation column bottom material supplying heat duty for the reboiler.

14. The process of claim 11 wherein at least a portion of the retentate stream is returned to the distillation column below the point of return of the upper stream that is not sent to the membrane.

* * * * *